(12) United States Patent
Edmunds

(10) Patent No.: US 10,383,775 B2
(45) Date of Patent: Aug. 20, 2019

(54) TAMPON ASSEMBLY

(71) Applicant: Kathleen Edmunds, Knoxville, TN (US)

(72) Inventor: Kathleen Edmunds, Knoxville, TN (US)

( * ) Notice: Subject to any disclaimer, the term of this patent is extended or adjusted under 35 U.S.C. 154(b) by 642 days.

(21) Appl. No.: 14/998,931

(22) Filed: Mar. 7, 2016

(65) Prior Publication Data

US 2016/0193089 A1    Jul. 7, 2016

Related U.S. Application Data

(63) Continuation-in-part of application No. 13/507,883, filed on Aug. 3, 2012, now Pat. No. 9,357,982.

(51) Int. Cl.
| | |
|---|---|
| *A61F 13/20* | (2006.01) |
| *A61F 13/34* | (2006.01) |
| *A61B 10/02* | (2006.01) |
| *A61B 10/00* | (2006.01) |

(52) U.S. Cl.
CPC .......... *A61F 13/2031* (2013.01); *A61B 10/02* (2013.01); *A61B 10/0291* (2013.01); *A61F 13/208* (2013.01); *A61F 13/2045* (2013.01); *A61F 13/34* (2013.01); *A61B 2010/0074* (2013.01)

(58) Field of Classification Search
CPC .. A61F 13/20; A61F 13/2031; A61F 13/2045; A61F 13/208; A61F 13/34; A61B 10/02; A61B 10/0291; A61B 2010/0074
USPC ............................. 604/385.17, 385.18, 904
See application file for complete search history.

(56) References Cited

U.S. PATENT DOCUMENTS

| | | | |
|---|---|---|---|
| 2,087,610 A | 7/1937 | Scott | |
| 2,241,451 A | 5/1941 | Fist | |
| 2,823,669 A | 2/1958 | Kunnas, Jr. .................. | 128/837 |
| 3,128,767 A | 4/1964 | Nolan ........................... | 604/330 |
| 3,216,422 A | 11/1965 | Steiger et al. | |
| 3,983,874 A | 10/1976 | Davis et al. .................. | 604/330 |
| 3,986,511 A | 10/1976 | Olofsson et al. ............. | 604/366 |
| 4,311,543 A | 1/1982 | Strickman et al. ........... | 156/224 |
| 4,497,317 A | 2/1985 | Boschetti ...................... | 128/837 |
| 4,640,272 A | 2/1987 | Monett | |
| 4,821,741 A | 4/1989 | Mohajer | |
| 5,231,992 A | 8/1993 | Leon ............................. | 600/572 |

(Continued)

FOREIGN PATENT DOCUMENTS

WO     WO 02/40912 A2    5/2002

*Primary Examiner* — Jacqueline F Stephens
(74) *Attorney, Agent, or Firm* — Michael E. McKee

(57) ABSTRACT

A tampon assembly includes a substantially inflexible and relatively thin impermeable portion having two opposite side faces and an outer edge which is oval in shape and markedly oval in form so that the oval shape of the impermeable portion has a largest dimension as measured through the center of the impermeable portion and a smallest dimension as measured through the center of the impermeable portion, and the largest dimension is at least about 1.5 times the size of the smallest dimension. The assembly further includes an absorbent pad portion which is secured to one side face of the impermeable portion so that when the assembly is positioned within a user, the absorbent pad portion is positioned in a condition for absorbing fluids and the outer edge of the impermeable portion sealingly engages the walls of the vaginal canal.

18 Claims, 3 Drawing Sheets

(56) References Cited

U.S. PATENT DOCUMENTS

| | | | |
|---|---|---|---|
| 5,295,984 A | 3/1994 | Contente et al. | 604/317 |
| 5,718,675 A | 2/1998 | Leijd | |
| 5,928,184 A | 7/1999 | Etheredge et al. | 604/15 |
| 6,126,616 A | 10/2000 | Sanyai | |
| 6,168,609 B1 | 1/2001 | Kamen et al. | 606/193 |
| 6,332,878 B1 * | 12/2001 | Wray | A61F 6/08 |
| | | | 128/830 |
| 6,796,973 B1 | 9/2004 | Contente et al. | |
| 7,824,383 B2 | 11/2010 | Sokal et al. | 604/285 |
| 2002/0026140 A1 | 2/2002 | McNamara | |
| 2005/0171455 A1 | 8/2005 | Turner | 600/569 |
| 2005/0256484 A1 | 11/2005 | Chase et al. | |

* cited by examiner

TAMPON ASSEMBLY

This is a continuation-in-part application of application Ser. No. 13/507,883, filed Aug. 3, 2012 and entitled TAMPON ASSEMBLY. The disclosure of this referenced application is incorporated herein by reference.

BACKGROUND OF THE INVENTION

This invention relates generally to feminine hygiene products and relates, more particularly, to tampon devices.

Inasmuch as tampon devices are commonly used by women to prevent the unwanted discharge of vaginal fluids through the vaginal canal, not all tampons of the prior art are equally-suited for this purpose. Firstly and in instances in which tampons comprised principally of a plug of absorbent material are used, the eventual saturation of the absorbent material prevents additional absorption of fluids. Therefore and in such instances, fluids are likely to migrate past such a tampon after the absorbent material becomes saturated. Secondly, there exists a diaphragm-class of tampon having a circular-shaped impervious membrane which is positionable within the vaginal canal for the intended purpose of preventing the passage of fluids which would otherwise flow through the canal. However, any poor fit-up between the edges of the membrane and the vaginal canal will not prevent the flow of fluids between the edge of the membrane and the walls of the canal and will, instead, likely promote user discomfort.

It would be desirable to provide a new and improved tampon assembly for preventing the unwanted discharge of vaginal fluids.

Accordingly, it is an object of the present invention to provide a new and improved tampon assembly which inhibits the flow of fluids through the vaginal canal.

Another object of the present invention is to provide such an assembly whose construction, including size and shape, facilitates the insertion of the assembly into place and the removal of the assembly following use.

Still another object of the present invention is to provide such an assembly which does not need to be compressed or folded upon itself during insertion of the assembly into place or during its removal following use.

Yet another object of the present invention is to provide such an assembly whose components provide an improved seal with the walls of the vaginal canal and effectively block the flow of fluids through the vaginal canal.

A further object of the present assembly is to provide such an assembly whose componentry is adapted to collect and absorb fluids when the assembly is used and readily accepts the opening-defining end of the cervix.

A still further object of the present invention is to provide such an assembly having a component which, if desired, can be recycled.

A yet further object of the present invention is to provide such an assembly which promotes user comfort, can be used for birth control purposes, and does not inhibit vaginal intercourse.

One more object of the present invention is to provide such an assembly which can be used as a substitute for a pessary to help support the vaginal walls against deformation or displacement due to prolapse of, for example, the bladder, cervix or rectum.

One more object of the present invention is to provide such an assembly which can be used for collecting cervical cells for laboratory (e.g. pap smear) testing purposes.

Still one more object of the present invention is to provide such an assembly which is uncomplicated in structure, yet effective in operation.

SUMMARY OF THE INVENTION

This invention resides in a tampon assembly positionable within the vaginal canal of a user wherein the vaginal canal has a posterior fornix and a sub-pubic portion and walls which extend between the posterior fornix and the sub-pubic portion of the canal.

The assembly includes a relatively thin and substantially inflexible saucer-shaped impermeable portion having two opposite concave and convex side faces and having an outer edge which is oval in shape and markedly elongate in form so that the oval shape of the impermeable portion has a largest dimension as measured across the center of the impermeable portion and a smallest dimension as measured across the center of the impermeable portion, and the largest dimension is at least about 1.5 times the smallest dimension so as to provide the impermeable portion with a length which corresponds to the largest dimension of the oval shape. The assembly also includes an absorbent portion which is secured to the concave side face of the impermeable portion so that when the tampon assembly is inserted lengthwise along the vaginal canal so that the largest dimension of the oval shape of the impermeable portion extends along the length of the vaginal canal, the smallest dimension of the oval shape of the impermeable portion, by virtue of the size of the smallest dimension, facilitates the lengthwise movement of the assembly along the length of the canal without requiring that the impermeable portion be compressed across the smallest dimension during insertion or during removal, and so that when the tampon assembly is positioned within the vaginal canal for use, the absorbent portion is in position to absorb fluids which exit the cervix and the outer edge of the impermeable portion is in sealing relationship with the vaginal walls of the user and the largest dimension of the oval shape of the impermeable portion enables the outer edge of the impermeable portion to engage the walls of the vaginal canal from the posterior fornix to the sub-pubic portion thereof. Furthermore, the impermeable portion possesses a degree of rigidity so that when the assembly is positioned into place within the vaginal canal, the assembly resists deformation and thereby renders the assembly capable of strengthening the vaginal walls, and the absorbent portion is sized to substantially fill the concave side face of the impermeable portion and to thereby enhance the fluid-absorbing capacity of the assembly.

DETAILED DESCRIPTION OF AN ILLUSTRATIVE EMBODIMENT

Figure 1:
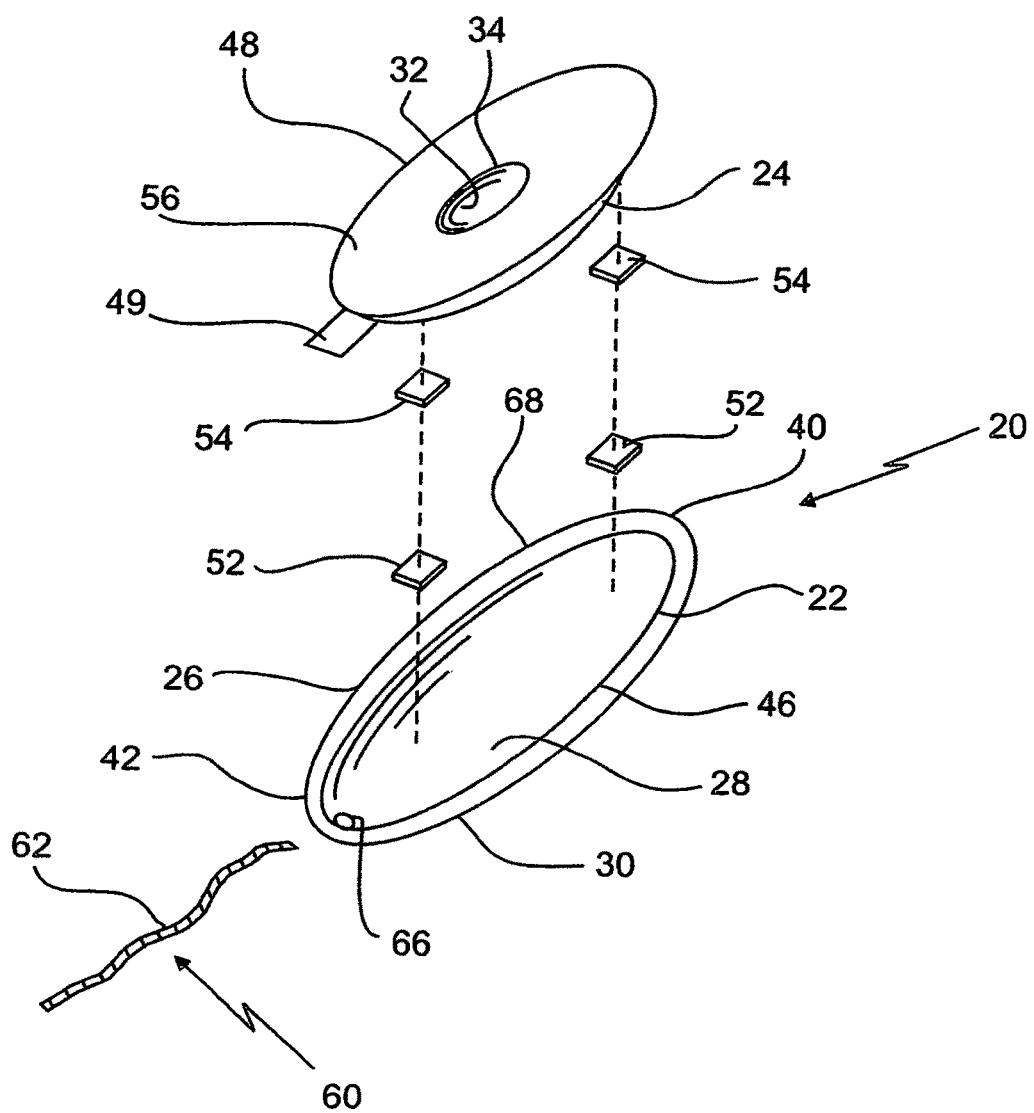
FIG. 1 is a perspective view of an embodiment of a tampon assembly within which features of the present invention are embodied and shown exploded.

Turning now to the drawings in greater detail and considering first FIG. 1, there is illustrated an embodiment, generally indicated 20, of a tampon assembly within which features of the present invention are embodied. The assembly 20 includes a liquid-impermeable portion 22 and an absorbent pad portion 24 which is releasably secured to the impermeable portion 22. As will be apparent herein, the absorbent portion 24 is adapted to absorb fluids which may exit the cervix of the user while the impermeable portion 22 of the tampon assembly 20 is adapted to provide a satisfactory seal between the outer edges of the impermeable portion 22 and the walls of the vaginal canal to prevent passage of fluids past the impermeable portion 22. In addition, the impermeable portion 22 is shaped and sized to facilitate the insertion of the assembly 22 into place within the vaginal canal for use and the removal of the assembly 20 from the vaginal canal following use without the need that the assembly 22, or more specifically, the impermeable portion 22 be compressed during insertion or removal.

Although the assembly 20 is primarily described herein as being used for preventing the discharge of fluids from the vaginal canal, the assembly 20 can also be used in applications in which it is desired to strengthen the vaginal walls (from the inside thereof) to prevent deformation or displacement thereof. For example, there exists physical conditions, such as bladder prolapse, cervical prolapse or rectum prolapse, characterized by the displacement of various organs from their normal positions and which, in some instances, bear upon the vaginal walls. To counter the deleterious effects of such physical conditions, the assembly 20 can be positioned in its desired position along the vaginal canal to strengthen the walls of the vaginal canal and thereby resist displacement of the organs. Accordingly, the assembly 20 can be used as a substitute for a pessary which might otherwise be used as an aid in this regard.

Furthermore and because cervical cells are likely to accumulate, over a period of time, upon the surface of the absorbent portion 22 during use of the assembly 20, the assembly 20 can provide a means by which cervical cells of a patient are obtained for laboratory (e.g. pap smear) testing purposes. Accordingly, the principles of the present invention can be variously applied.

With reference to FIGS. 1-4, the impermeable portion 22 is saucer-shaped in form having a relatively shallow, concave side face 28 and an opposite convex side face 30. In addition, the impermeable portion 22 is relatively thin as measured between the side faces 28, 30. Moreover, the impermeable portion 22 is substantially inflexible in nature so as to provide a degree of stiffness or rigidity to the assembly 20 when positioned in place within the vaginal canal for use. As will be apparent herein, the stiffness or rigidity of the impermeable portion 22 is advantageous in that it helps to rigidify the assembly 20 and strengthen the walls of the user's vaginal canal when the assembly 20 is positioned therein.

To provide the impermeable portion 22 with a desired degree of inflexibility, the impermeable portion 22 can be constructed of any of a number of elastomeric materials, such as a relatively hard plastic (which can include silicon), or other classes of materials, such as a coated paper. However, it may be preferable to avoid latex as a choice of material for the impermeable portion 22 due to the allergic reaction that some individuals have to that material.

It is a feature of the assembly 20 that its impermeable portion 22 has a markedly oval-shaped outer edge 26 (defining an inwardly-directed lip 27) to provide a better-fitting relationship between the outer edge 26 and the walls of the vaginal canal than can be had with circular-shaped portions of diaphragm-class of tampons of the prior art. In this connection, applicant, who is an obgyn physician, has discovered that in most females whom she has examined, the anterior-posterior dimension of the pelvis is greater than the transverse diameter of the pelvis. In other words and in order for the impermeable portion 22 to suitably fit within the vaginal canal and provide a desirable and comfortable sealing relationship with the walls of the canal, applicant has discovered that the front-to-back dimension of the impermeable portion 22 should be larger than the side-to-side dimension of the impermeable portion 22.

More specifically, the outer edge 26 of the impermeable portion 22 of the depicted assembly 20 (as best viewed in FIG. 3) is shaped to resemble an oval of markedly elongate form so that its maximum dimension (as measured along its major, or longitudinal, axis 36, indicated in phantom and extending through the center of the oval shape of the outer edge 26) is at least about 1.5 times the size of the minimum dimension (as measured along its minor axis 38, also indicated in phantom and extending through the center of the oval shape of the outer edge 26). Preferably, the oval-shaped outer edge 26 has a maximum dimension which is at least about 2.0 times the size of its minimum dimension. It has been found that the depicted assembly 20, with its oval-shaped impermeable portion 22, provides a better edge-to-vaginal canal sealing relationship than is capable of being formed with any impermeable portion of circular form and is advantageous in this respect.

While an oval, by definition, is symmetrical about at least one of its major or minor axes, the oval shape of the depicted impermeable portion 22 is symmetrical about each of its major and minor axes 36, 38. Therefore and more particularly, the shape of the outer edge 26 of the depicted impermeable portion 22 is elliptical. In a broad sense, therefore, the outer edge 26 of the impermeable portion 22 is oval, but in a preferred embodiment of the assembly 20, the outer edge 26 of the impermeable portion 22 is elliptical in shape.

Moreover and as used herein, the descriptive phrase "oval shape of markedly elongate form" is intended to differentiate the shape of the impermeable portion 22, or more specifically, that of the outer edge 26, from shapes which could be described as circular, near-circular, or even egg-shaped in form. In other words, the impermeable portion 22 is shaped to provide its outer edge 26 with an appearance which is distinctively elongate, and such a distinctively elongate appearance is described herein in structural terms by way of the stated requirement that the maximum diameter of the impermeable portion 22 as measured along its major axis 36 is at least 1.5 times the size of the minimum dimension of the impermeable portion 22 as measured along its minor axis 38.

The assembly 20, and more specifically, the impermeable portion 22, is intended to be inserted endwise, or lengthwise, into place through the vaginal canal as the impermeable portion 22 is directed and moved lengthwise (i.e. in a direction parallel to the major axis 36) through the canal. Accordingly and for present purposes, the leading end of the impermeable portion 22 (i.e. the end of the impermeable portion 22 which is inserted first through the vaginal canal 22) is indicted 40 in FIGS. 1-4, the opposite, or trailing, end of the impermeable portion 22 (i.e. the end of the impermeable portion 22 which follows the leading end 40 into place) is indicated 42 in FIGS. 1-4, and the opposite sides of the impermeable portion 22 which extend between the leading and trailing ends 40 and 42 are indicated 44 and 46 in FIGS. 1 and 4.

With reference again to FIGS. 1-3, the absorbent portion 24 is comprised of a substantially platen arrangement of soft absorbent material, such as a layup of cotton, rayon or a cotton/rayon blend of fibers, and is positionable against the concave side face 28 of the impermeable portion 22 for securement thereto. As best shown in FIG. 1, the absorbent portion 24 has an outer edge 48 which is shaped similar (i.e. oval-shaped) to that of the outer edge 26 and is centrally-disposed against the side face 28 of the impermeable portion 22 so that the outer edge 48 is captured beneath the inwardly-directed lip 27 of the impermeable portion 22. Accordingly, the outer edge 48 of the absorbent portion 24 is slightly smaller in size than the outer edge 26 so that when positioned against the side face 28, no part of the absorbent portion 24 extends outboard of the outer edge 26. With the absorbent portion 24 positioned against the side face 28, the total thickness of the assembly 20, as measured at its thickest point, is preferably no more than about 2.0 cm.

In addition, there is provided in the upwardly-facing surface, indicated 56, of the absorbent portion 22 a preformed concave indentation 32 which is centrally disposed therein. Within the depicted assembly 20, the concave indentation 32 has an outer, oval-shaped edge 34 which is concentrically-arranged within the outer edge 26 of the impermeable portion 22 and possesses a dimension along each of its major and minor axes which is about one-third the size of the corresponding major or minor axis 36 or 38 of the outer edge 32. Meanwhile, the depth of the concave indentation 34 (as measured from the plane of the surface 56) is about one centimeter, but the indentation 34 can possess an alternative depth.

If desired, the absorbent portion 24 can also be provided with a pull tab 49 disposed adjacent one end thereof for facilitating a removal of the absorbent portion 24 from the impermeable portion 22 following use of the assembly 20.

It is also a feature of the assembly 20 that it includes means, generally indicated 50, for releasably securing the absorbent portion 24 to the concave side face 28 of the impermeable portion 22 so that during use of the assembly 20, the impermeable portion 22 remains securely attached to the side face 28 and so that following the withdrawal of the assembly 20 from a vaginal canal, the absorbent portion 24 can be readily separated from the impermeable portion 22 (by, for example, pulling upon the pull tab 49) so that the absorbent portion 24 can be discarded and the impermeable portion 22, if desired, can be recycled.

Within the depicted assembly 20 and with reference again to FIG. 1, the securing means 50 is in the form of a hook and loop type fastener (such as is available under the trade designation Velcro) including hook-providing portions 52 and loop-providing portions 54, which are attached to the impermeable portion 22 and the absorbent portion 24 for securing the absorbent portion 24 to the impermeable portion 22. More specifically, two hook-providing portions 52 are attached, as with glue, to the side face 28 of the impermeable portion 22, and two loop-providing portions 54 are attached, as with glue, to the underside of the absorbent portion 24 so that upon pressing the absorbent portion 24 against the side face 28, the hook-providing and loop-providing portions 52, 54 cooperate to securely, yet releasably, attach the absorbent portion 24 to the impermeable portion 22.

Figure 2:
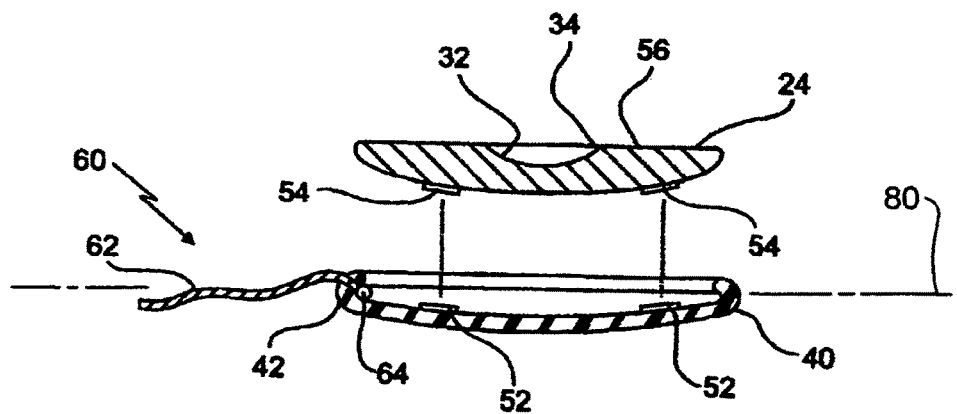
FIG. 2 is a longitudinal cross-sectional view of the FIG. 1 assembly, shown exploded.
Figure 3:
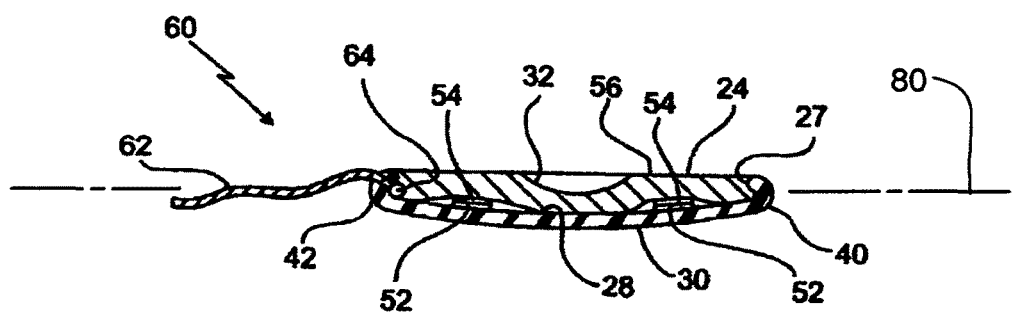
FIG. 3 is a longitudinal cross-sectional view of the FIG. 1 assembly, shown assembled.
Figure 4:
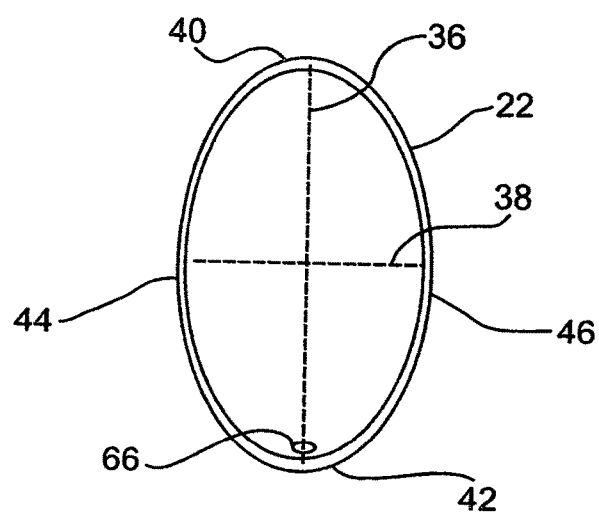
FIG. 4 is a plan view of the impermeable portion of the FIG. 1 assembly as seen generally from above in FIG. 1.

It is an additional feature of the assembly 20 that it also includes means, generally indicated 60 in FIGS. 1 and 2, for facilitating the removal of the assembly 20 from its position of use within the vaginal canal. Within the depicted assembly 20, the facilitating means 60 includes a length of cord or string 62 comprised, for example, of cotton, and which is securely tied or otherwise secured, as with a knot 64 (FIGS. 2 and 3), to the impermeable portion 22 adjacent the trailing end 42 thereof. To facilitate the passing of the string 62 through the impermeable portion 22 for purposes of tying or knotting the string 62, the impermeable portion 22 is provided with a through-opening 66 (FIGS. 1 and 4) adjacent the trailing edge 42 thereof. Because the trailing end 42 of the impermeable portion 22 has been described above as being the end of the impermeable portion 22 which follows the leading end 40 of the impermeable portion 22 into the vaginal canal during installation, the trailing edge 42 is the first end of the impermeable portion 22 which exits the vaginal canal when withdrawn from the user. This being the case, the string 62 provides a visual indication to the user as to which end of the impermeable portion 22 corresponds with the trailing end 24 thereof.

If desired, the entirety of the assembly 20 (i.e. its impermeable portion 22 and absorbent portion 24) can be coated with a thin coating 68 (FIG. 1) of lubricant, such as petroleum jelly, to facilitate the insertion and removal of the assembly 20.

Figure 5:
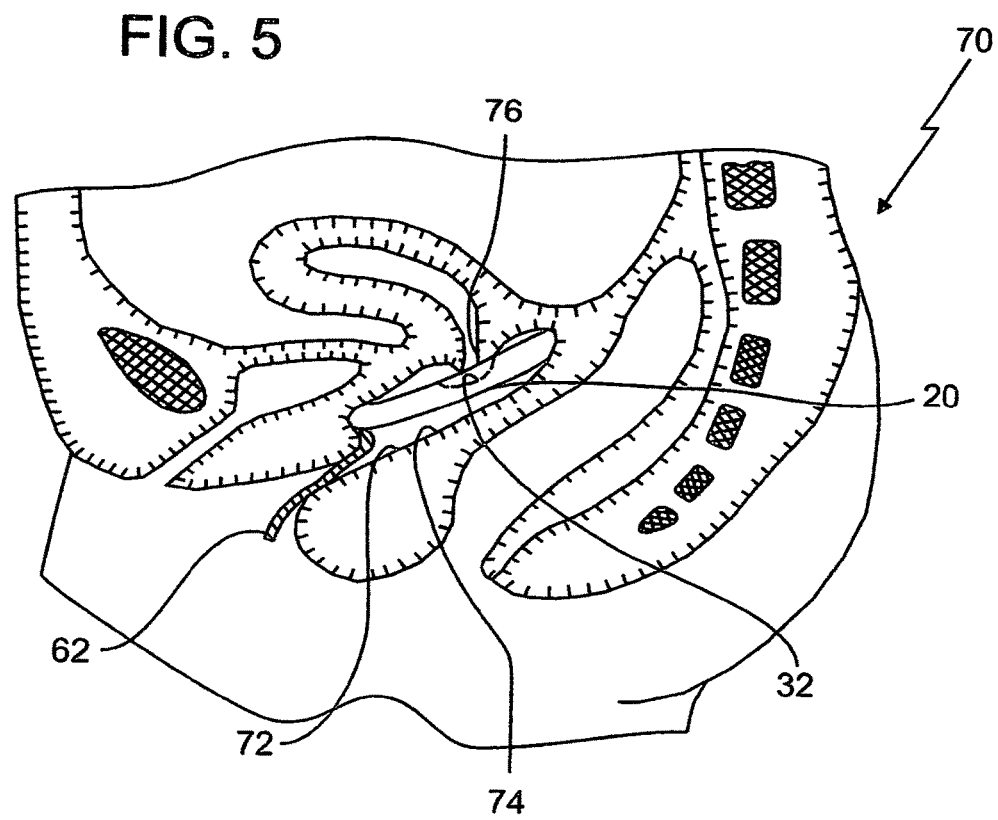
FIG. 5 is a cross-sectional view illustrating schematically the manner in which the FIG. 1 assembly is positioned for use.

With reference to FIG. 5, there is schematically illustrated a cross-sectional portion, indicated 70, of the female anatomy within which the FIG. 1 assembly 20 can be positioned for use. More specifically, the depicted portion 70 includes a vaginal canal 72 having tubular walls 74 and a cervix 76 disposed adjacent the distal, or rearward, end of the vaginal canal 72. When fully positioned within the vaginal canal 72, the outer edge 26 of the impermeable portion 22 bears and rests against the vaginal walls 74 from about the posterior fornix (the vaginal region disposed rearwardly of the cervix 76) to the sub-pubic portion of the upper vaginal wall (i.e. a location disposed immediately behind the pubic bone) and the opening-defining end of the cervix 76 is accepted by the concave indentation 32 of the absorbent portion 24.

As suggested earlier, the assembly 22 is inserted into place into the vaginal canal for use as the impermeable portion 22 is directed endwise (i.e. first end 40-first) into and through the vaginal canal 72. The relatively small size of the smallest dimension (i.e. as measured across the minor axis 38) of the oval-shaped impermeable portion 22 in comparison to the size of the largest, or lengthwise, dimension (i.e. as measured across the major axis 36) of the impermeable portion 22 facilitates the lengthwise movement of the assembly 20 along the canal without requiring that the impermeable portion 22 be compressed across the smallest dimension during insertion of the assembly 20 into place or during removal of the assembly 20 following use.

With the assembly 20 disposed in position within the vaginal canal 72 for use, the contributions of the oval shape of the outer edge 26 of the impermeable portion 22 and the engagement of the outer edge 26 against the vaginal walls 74 places the outer edge 26 of the impermeable portion 22 in satisfactory sealing relationship with the vaginal walls 74. Furthermore, any discharge from the cervix 76 (whose opening-defining end effectively self-centers itself within the concave indentation 32) is permitted to pool or collect within the indentation 32 for absorption by the material of the absorbent portion 24. Therefore and during use, the absorbent portion 22 is in position to absorb fluid discharged from the cervix 76, even though the cervix 76 is not encapsulated by (the outer edges 26) of the impermeable portion.

Moreover, as the absorbent portion 24 is permitted to expand due to its absorption of fluids exiting the cervix 76, the absorbent portion 24 is prevented from expanding in every direction with respect to the vaginal canal 72, and instead, its expansion is confined to a direction which is substantially away from the concave side face 28. More specifically, the absorbent portion 24 is prevented from expanding laterally with respect to the vaginal canal 72 when the assembly 20 is positioned therein. This feature is believed to be due, at least in part, to the fact that the impermeable portion 22, by virtue of its inflexible nature, prevents the absorbent portion 24 from expanding in any direction other than in a direction which is substantially normal to the concave side face 28. Compared to a prior art absorbent device which tends to expand in every direction (including laterally) with respect to a vaginal canal within which the device is positioned—and commonly must necessarily be folded upon itself to be removed from the canal, the impermeable portion 22 of applicant's assembly 20 prohibits the absorbent portion 24 from expanding laterally within a vaginal canal and is advantageous in this respect. If desired, the absorbent portion 24 can be coated with a spermicide and left in place for a prolonged period of time (e.g. up to about six hours) following intercourse for added birth control.

The shape and inflexible nature of the impermeable portion 22 is also advantageous when positioned into place within the vaginal canal 72 from the standpoint of user comfort. In this connection and with reference again to FIGS. 2 and 3, the outer edge 26 lies substantially within a plane 80 and since the impermeable portion 22 is substantially inflexible in shape, the outer edge 26 engages the tubular walls 74 of the vaginal canal 72 along points therealong which collectively conform to the oval shape of the outer edge 26 and thereby enhance user comfort. In other words and because of the inflexibility and oval shape of the outer edge 26, the tubular walls 74 are not distended laterally by any appreciable extent while maintaining sealing engagement with the tubular walls 74 along a plane.

The resultant engagement between the tubular walls 74 of the vaginal canal 72 and the planar outer edge 26 of the impermeable portion 22 is preferable over that which would result from either an inflexible impermeable portion having a circular edge or a flexible impermeable portion which assumes a collapsed or folded condition when positioned within the vaginal canal. For example, in the instance in which the outer edge of an inflexible impermeable portion is circular, the vaginal walls would necessarily distend laterally by an amount equal to the diameter of the circular outer edge and not provide as effective of a seal with the outer edge of the impermeable portion; and in the instance in which the outer edges of an impermeable portion is permitted to assume a collapsed or folded condition when positioned within the vagina canal, the resulting engagement between the tubular walls of the vaginal canal and the folded outer edge would not likely be confined to a plane.

As suggested earlier, the removal of the assembly 20 from the vaginal canal 72 is facilitated by the string 62 which can be pulled upon by the user, and the impermeable portion 22 does not have to be squeezed or compressed from side-to-side in order to remove the assembly 20 from the canal 72. Furthermore and upon removal of the assembly 20 from the vaginal canal 72, the absorbent portion 24 can be separated from the impermeable portion 22 by pulling the components 22 and 24 apart (so that the hook-bearing portions 52 and loop-bearing portions 54 are separated from one another) for disposal of the absorbent portion 24 and, if desired, for recycling of the impermeable portion 22.

The tampon assembly 20 can be constructed in any of a number of sizes to accommodate a range of vaginal sizes. For example, the impermeable portion 22 can be sized so that it measures about 65 mm, 75 mm or 85 mm along its major axis 38 to accommodate vaginal canals of different sizes.

It will be understood that numerous modifications and substitutions can be had to the aforedescribed embodiment 20 without departing from the spirit of the invention. Accordingly, the aforedescribed embodiment 20 is intended for the purpose of illustration and not as limitation.

The invention claimed is:

1. A tampon assembly configured to be inserted and positioned in place for use along the length of the vaginal canal of a user and to be removed following use, the assembly comprising:
   a thin saucer-shaped impermeable portion configured to be inserted within and extend along the length of a vaginal canal, wherein the impermeable portion has two opposite concave and convex side faces and has an outer edge which is oval in shape and markedly elongate in form so that the oval shape of the impermeable portion has a largest dimension as measured across the center of the impermeable portion and a smallest dimension as measured across the center of the impermeable portion, and the largest dimension is at least about 1.5 times the smallest dimension so as to provide the impermeable portion with a length which corresponds to the largest dimension of the oval shape; and
   an absorbent portion secured to the concave side face of the impermeable portion and so that when the impermeable portion is inserted lengthwise into place, the largest dimension of the oval shape of the impermeable portion extends along the length of the vaginal canal, and the smallest dimension of the oval shape of the impermeable portion, by virtue of the size of the smallest dimension, facilitates the lengthwise movement of the impermeable portion into place without requiring that the impermeable portion be compressed across the smallest dimension during insertion or during removal, and the impermeable portion, with the absorbent portion secured thereto, is configured to be positionable into place so that the absorbent portion is in position to absorb fluids which exit the cervix; and
   the impermeable portion possesses a degree of rigidity so that when the assembly is positioned into place for use, the assembly resists deformation; and
   the absorbent portion is sized to fill the concave side face of the impermeable portion and to thereby enhance the fluid-absorbing capacity of the assembly;
   wherein the absorbent portion is platen in shape and has an outer edge, and wherein the absorbent portion is positioned against the concave side face of the impermeable portion in a concentric relationship with the outer edge of the impermeable portion and possesses no part which extends outboard of the outer edge of the impermeable portion; and
   wherein the impermeable portion includes an inwardly-directed lip which extends along the outer edge of the impermeable portion, and the absorbent portion is captured by the inwardly-directed lip.

2. The assembly as defined in claim 1 wherein the largest dimension is about 2.0 times the smallest dimension.

3. The assembly as defined in claim 1 wherein the outer edge of the impermeable portion is elliptical in shape.

4. The assembly as defined in claim 1 wherein the outer edge of the impermeable portion is sized and configured to surround the cervix when the assembly is positioned into place.

5. The assembly as defined in claim 1 further comprising means for releasably securing the absorbent portion to the concave side face of the impermeable portion.

6. The assembly as defined in claim 5 wherein the means for releasably securing includes a hook and loop fastener including a hook-providing portion and a loop-providing portion, and one of the hook-providing portion and the loop-providing portion is attached to the impermeable portion and the other of the hook-providing portion and the loop-providing portion is attached to the absorbent portion.

7. The assembly as defined in claim 1 further comprising an amount of lubricant which is coated about the impermeable and absorbent portions.

8. The assembly as defined in claim 1 wherein the absorbent portion has a side surface which faces away from the concave side face of the impermeable portion, and the side surface defines a concave indentation therein which is centrally disposed therein.

9. A tampon assembly configured to be inserted and positioned in place for use along the length of a vaginal canal and to be removed following use and configured to be positioned adjacent the cervix of a user, said assembly comprising:
 a thin, saucer-shaped impermeable portion configured to be inserted and positioned within and extend along the length of the vaginal canal, wherein the impermeable portion has two opposite side faces wherein one of the side faces is concave in form and has an outer edge which is oval in shape and markedly elongate in form so that the oval shape of the impermeable portion has a largest dimension as measured across the center of the impermeable portion and a smallest dimension as measured through the center of the impermeable portion, and the largest dimension is at least about 1.5 times the size of the smallest dimension so as to provide the impermeable portion with a length which corresponds to the largest dimension of the oval shape; and
 an absorbent pad portion which is secured to the one concave side face of the impermeable portion and so that when the impermeable portion is inserted lengthwise into place, the largest dimension of the oval shape of the impermeable portion extends along the length of the vaginal canal and the smallest dimension of the oval shape of the impermeable portion, by virtue of the size of the smallest dimension, facilitates the lengthwise movement of the impermeable portion into place without requiring that the impermeable portion be compressed across the smallest dimension during insertion or removal, and so that when the assembly is positioned into place for use, the absorbent pad portion is disposed between the cervix and the impermeable portion for absorbing fluids which exit the cervix; and
 the impermeable portion is constructed of a material which provides the assembly with a degree of rigidity to resist deformation; and
 the absorbent pad portion is sized to a fill the concave side face of the impermeable portion and to thereby enhance the fluid-absorbing capacity of the assembly;
 wherein the absorbent pad portion is platen in shape and has an outer edge, and wherein the absorbent pad portion is positioned against the concave side face of the impermeable portion in a concentric relationship with the outer edge of the impermeable portion and possesses no part which extends outboard of the outer edge of the impermeable portion; and
 wherein the impermeable portion includes an inwardly-directed lip which extends along the outer edge of the impermeable portion, and the absorbent portion is captured by the inwardly-directed lip.

10. The assembly as defined in claim 9 wherein the largest dimension is about 2.0 times the smallest dimension.

11. The assembly as defined in claim 9 wherein the outer edge of the impermeable portion is elliptical in shape.

12. The assembly as defined in claim 9 further comprising means for releasably securing the absorbent pad portion to the concave side face of the impermeable portion.

13. The assembly as defined in claim 9 further comprising an amount of lubricant which is coated about the impermeable and absorbent portions.

14. The assembly as defined in claim 9 wherein the impermeable portion includes a leading end which is configured to first enter the vaginal canal when the impermeable portion is inserted into place and an opposite trailing end, and the assembly further includes a cord which is securely attached to the impermeable portion adjacent the trailing end thereof for facilitating the removal of the assembly following use.

15. The assembly as defined in claim 9 wherein the absorbent pad portion has a side surface which faces away from the one side face of the impermeable portion, and the side surface defines a concave indentation therein which is centrally disposed therein.

16. A tampon assembly configured to be inserted and positioned into place for use along the length of a user's vaginal canal having walls and to be removed following use and configured to be positioned adjacent the cervix to resist deformation of the vaginal canal walls or for collecting cervical cells for laboratory testing purposes the assembly comprising:
 a thin, saucer-shaped impermeable portion configured to be inserted within and extend along the length of the vaginal canal and to engage the walls of the vaginal canal when inserted therein, wherein the impermeable portion has two opposite side faces wherein one of the side faces is concave in form and has an outer edge which is oval in shape and markedly elongate in form so that the oval shape of the impermeable portion has a largest dimension as measured across the center of the impermeable portion and a smallest dimension as measured across the center of the impermeable portion, and the largest dimension is at least about 1.5 times the size of the smallest dimension so as to provide the impermeable portion with a length which corresponds to the largest dimension of the oval shape; and
 an absorbent pad portion which is secured to the one concave side face of the impermeable portion and so that when the impermeable portion is positioned into place for use, the absorbent pad portion is disposed between the cervix and the impermeable portion;
 wherein the absorbent portion has a side surface which faces away from the one concave side face of the impermeable portion, and the side surface defines a concave indentation therein which is centrally disposed therein; and
 wherein the impermeable portion includes a leading end which is configured to first enter the vaginal canal when the impermeable portion is inserted into place and an opposite trailing end so that when the impermeable portion is inserted lengthwise into place for use, the smallest dimension of the oval shape of the impermeable portion, by virtue of the size of the smallest dimension, facilitates the lengthwise movement of the impermeable portion without requiring that the impermeable portion be compressed across the smallest dimension during insertion or during removal and so that when the impermeable portion is positioned into place for use, the largest dimension of the oval shape of the impermeable portion extends along the length of the vaginal canal, and the assembly further includes a cord which is securely attached to the impermeable portion adjacent the trailing end thereof for facilitating the removal of the assembly following use; and the impermeable portion provides the assembly with a degree of rigidity so that when the assembly is inserted into place for use, the assembly resists deformation; and the absorbent pad portion is sized to fill the concave side face of the impermeable portion;

wherein the absorbent pad is platen in shape and has an outer edge, and wherein the absorbent pad portion is positioned against the concave side face of the impermeable portion in a concentric relationship with the outer edge of the impermeable portion and possesses no part which extends outboard of the outer edge of the impermeable portion; and wherein the impermeable portion includes an inwardly-directed lip which extends along the outer edge of the impermeable portion, and the absorbent portion is captured by the inwardly-directed lip.

17. The assembly as defined in claim 16 further comprising means for releasably securing the absorbent pad portion to the concave side face of the impermeable portion.

18. A tampon assembly comprising:

a thin saucer-shaped impermeable portion having two opposite concave and convex side faces and having an outer edge which is oval in shape and markedly elongate in form so that the oval shape of the impermeable portion has a largest dimension as measured across the center of the impermeable portion and a smallest dimension as measured across the center of the impermeable portion, and the largest dimension is at least about 1.5 times the smallest dimension so as to provide the impermeable portion with a length which corresponds to the largest dimension of the oval shape; and an absorbent portion secured to the concave side face of the impermeable portion; and the impermeable portion being insertable lengthwise into place, and the smallest dimension of the oval shape of the impermeable portion, by virtue of the size of the smallest dimension, facilitates the lengthwise movement of the impermeable portion into place without requiring that the impermeable portion be compressed across the smallest dimension during insertion or during removal; and the impermeable portion possesses a degree of rigidity so that when the assembly is positioned into place for use, the assembly resists deformation; and the absorbent portion is sized to fill the concave side face of the impermeable portion and to thereby enhance the fluid-absorbing capacity of the assembly;

wherein the absorbent pad portion is platen in shape and has an outer edge, and wherein the absorbent portion is positioned against the concave side face of the impermeable portion in a concentric relationship with the outer edge of the impermeable portion and possesses no part which extends outboard of the outer edge of the impermeable portion; and wherein the impermeable portion includes an inwardly-directed lip which extends along the outer edge of the impermeable portion, and the absorbent portion is captured by the inwardly-directed lip.

* * * * *